US010661027B2

(12) United States Patent
Aneas

(10) Patent No.: US 10,661,027 B2
(45) Date of Patent: May 26, 2020

(54) SYRINGE COMPRISING A BONDED NEEDLE

(71) Applicant: BIOCORP PRODUCTION, Issoire (FR)

(72) Inventor: Antoine Aneas, Menetrol (FR)

(73) Assignee: BIOCORP PRODUCTION, Issoire (FR)

( * ) Notice: Subject to any disclaimer, the term of this patent is extended or adjusted under 35 U.S.C. 154(b) by 108 days.

(21) Appl. No.: 15/738,667

(22) PCT Filed: Jun. 22, 2016

(86) PCT No.: PCT/EP2016/064374
§ 371 (c)(1),
(2) Date: Dec. 21, 2017

(87) PCT Pub. No.: WO2016/207196
PCT Pub. Date: Dec. 29, 2016

(65) Prior Publication Data
US 2018/0177955 A1    Jun. 28, 2018

(30) Foreign Application Priority Data
Jun. 23, 2015  (FR) ..................... 15 55748

(51) Int. Cl.
*A61M 5/34*   (2006.01)
*A61M 5/32*   (2006.01)
(Continued)

(52) U.S. Cl.
CPC ............ *A61M 5/344* (2013.01); *A61M 5/178* (2013.01); *A61M 5/31583* (2013.01);
(Continued)

(58) Field of Classification Search
CPC combination set(s) only.
See application file for complete search history.

(56) References Cited

U.S. PATENT DOCUMENTS

2009/0299295 A1    12/2009  Rubinstein et al.
2011/0137261 A1     6/2011  Garber et al.
(Continued)

FOREIGN PATENT DOCUMENTS

SU           1727826 A1    4/1992
WO       2007077463 A1    7/2001
(Continued)

OTHER PUBLICATIONS

International Search Report for PCT/EP2016/064374 dated Aug. 31, 2016.

*Primary Examiner* — Bhisma Mehta
*Assistant Examiner* — Hamza A Darb
(74) *Attorney, Agent, or Firm* — Pearne & Gordon LLP

(57) ABSTRACT

A syringe having a bonded needle, comprising a syringe body, a needle protector comprising a flexible cap, an outer sleeve, which can move along a longitudinal axis between an extended position, in which it covers the needle, and a retracted position, in which it does not cover the needle, and a collar, which is mounted with a radial clearance around an end part of the syringe body and which comprises at least one pin engaged in a guide opening of the sleeve. A portion of the flexible cap fills the radial clearance between the end part of the syringe body and the collar when the cap is mounted on the syringe, such that the collar cannot rotate around the end part of the syringe body as long as the cap is mounted on the syringe.

11 Claims, 9 Drawing Sheets

Figure 1:
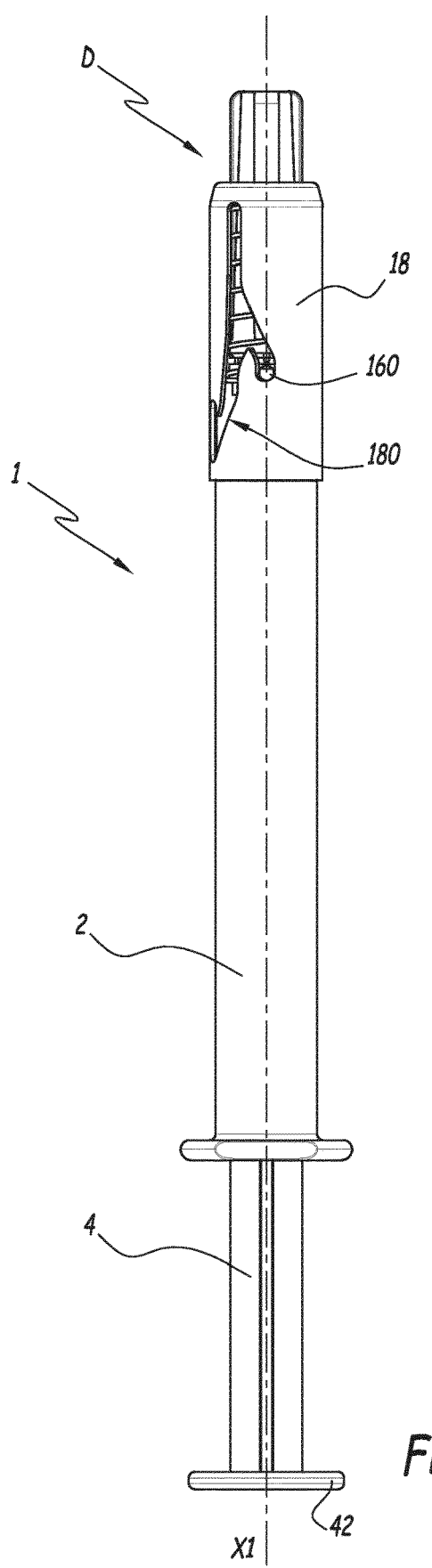

(51) Int. Cl.
*A61M 5/178* (2006.01)
*A61M 5/315* (2006.01)

(52) U.S. Cl.
CPC .......... *A61M 5/3204* (2013.01); *A61M 5/326* (2013.01); *A61M 5/3272* (2013.01); *A61M 5/347* (2013.01); *A61M 2005/3267* (2013.01); *A61M 2205/0216* (2013.01)

(56) References Cited

U.S. PATENT DOCUMENTS

| | | | |
|---|---|---|---|
| 2012/0316508 A1* | 12/2012 | Kirchhofer | A61M 5/31553 604/198 |
| 2014/0039407 A1* | 2/2014 | Schoonmaker | A61M 5/3202 604/198 |
| 2015/0018773 A1 | 1/2015 | Evans et al. | |
| 2015/0190586 A1* | 7/2015 | Takemoto | A61M 5/3213 604/198 |

FOREIGN PATENT DOCUMENTS

| | | |
|---|---|---|
| WO | 2009/137845 A1 | 11/2009 |
| WO | 2013/134465 A1 | 9/2013 |
| WO | 2015022787 A1 | 2/2015 |

\* cited by examiner

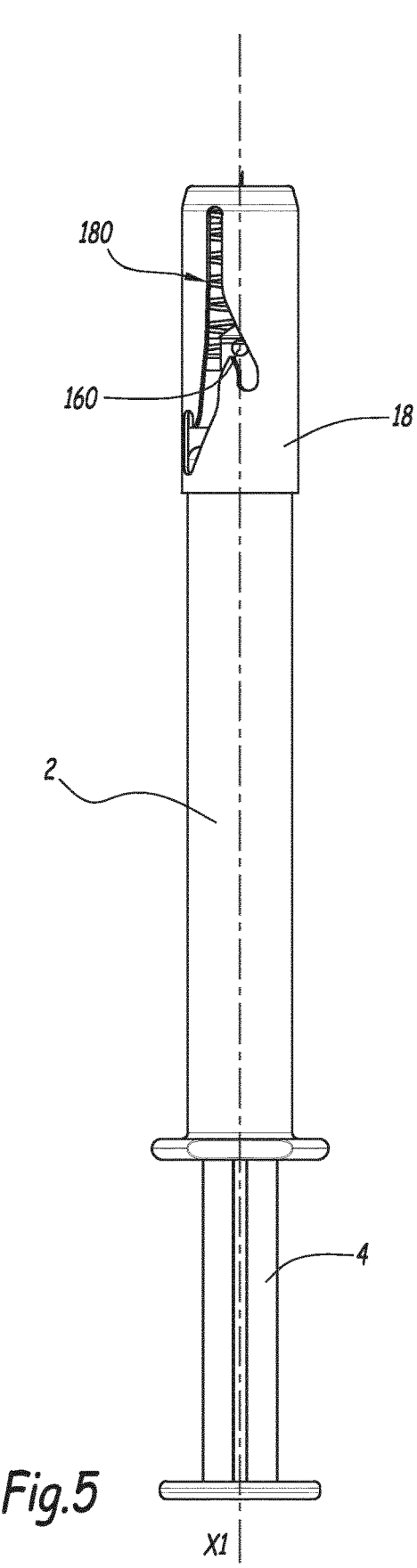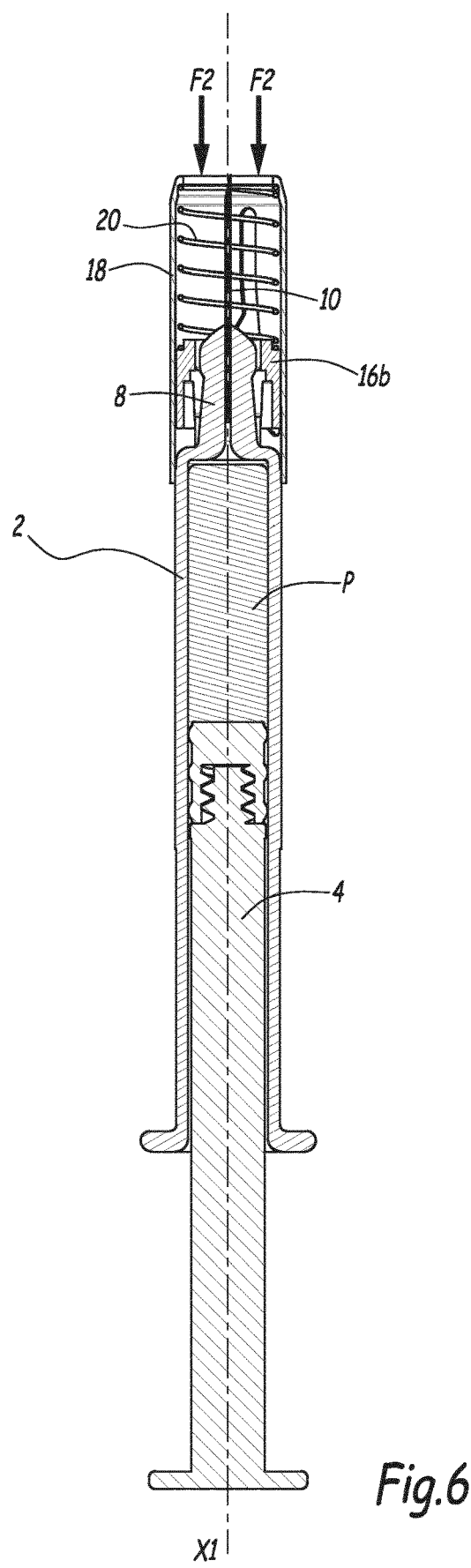

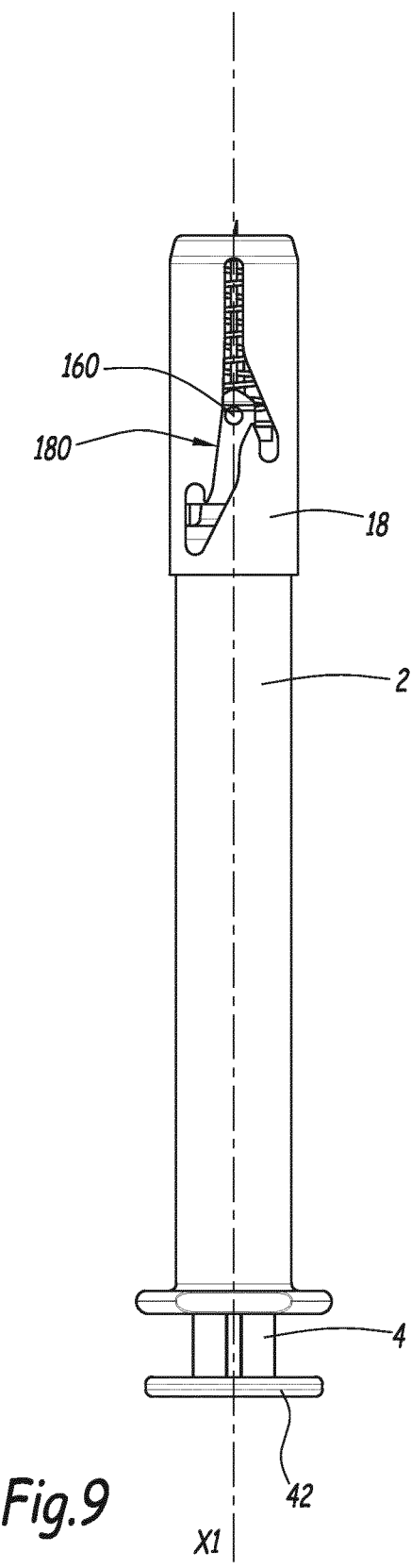
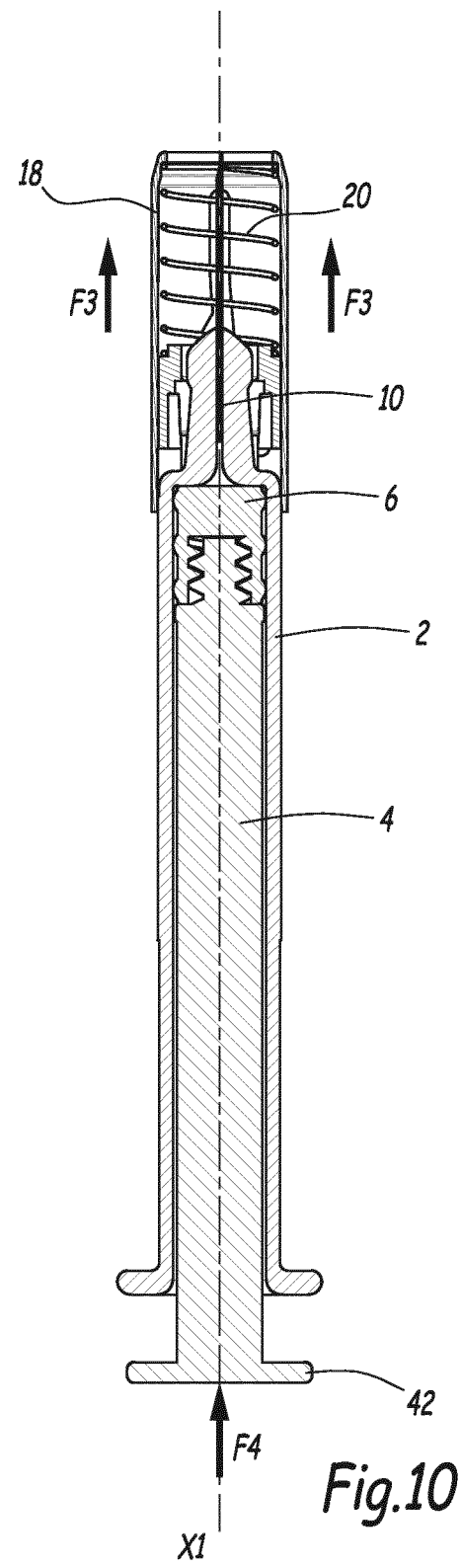

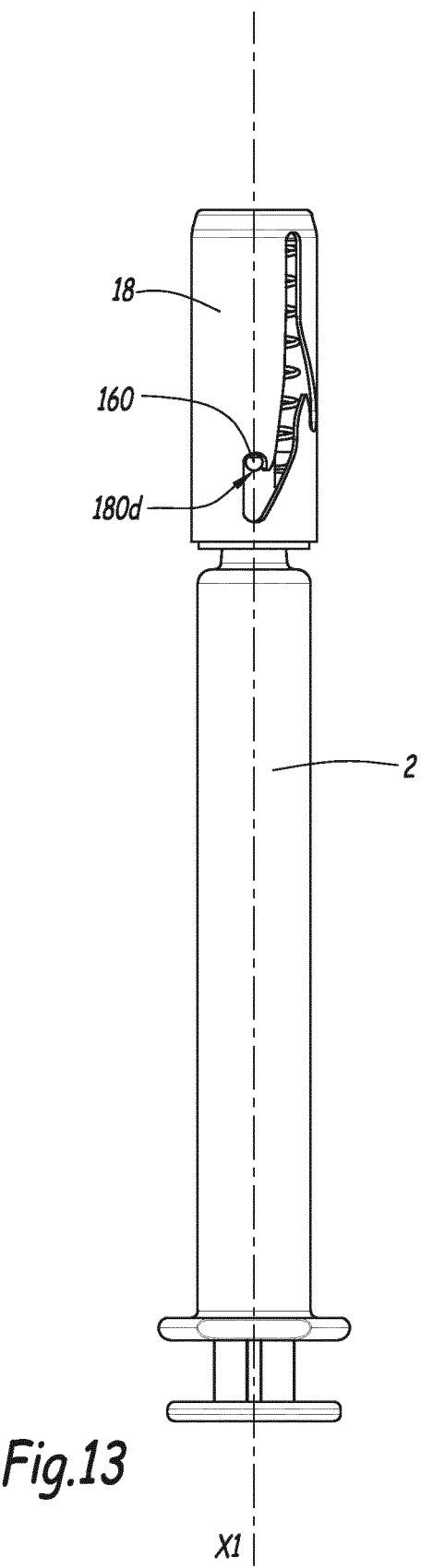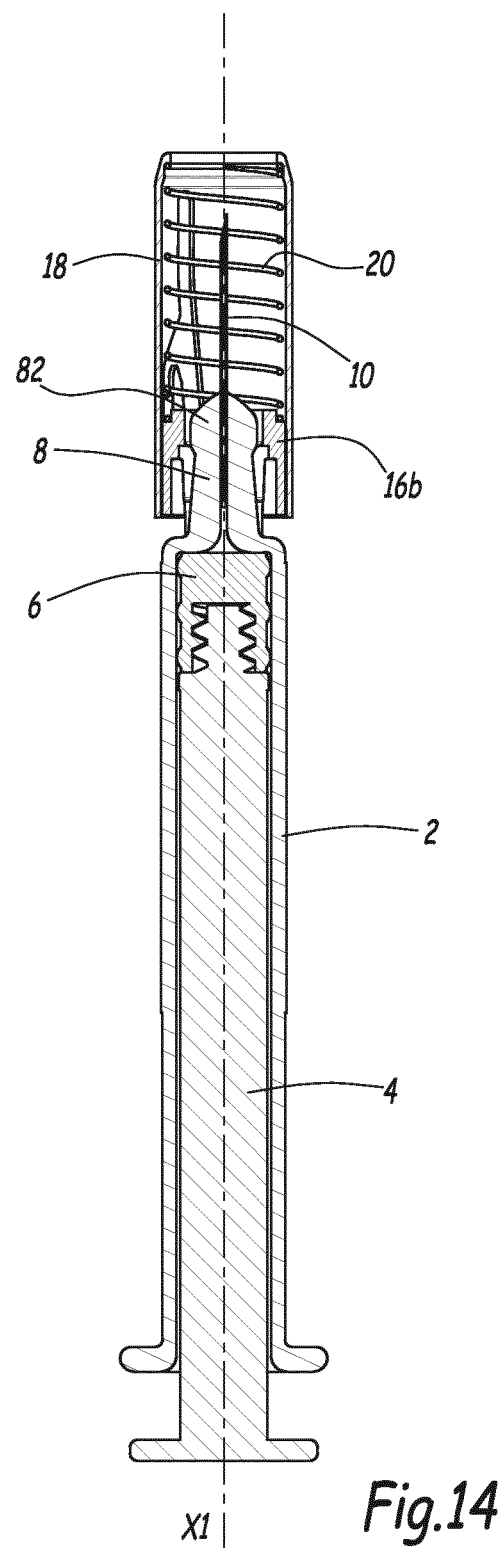
Fig.13
Fig.14

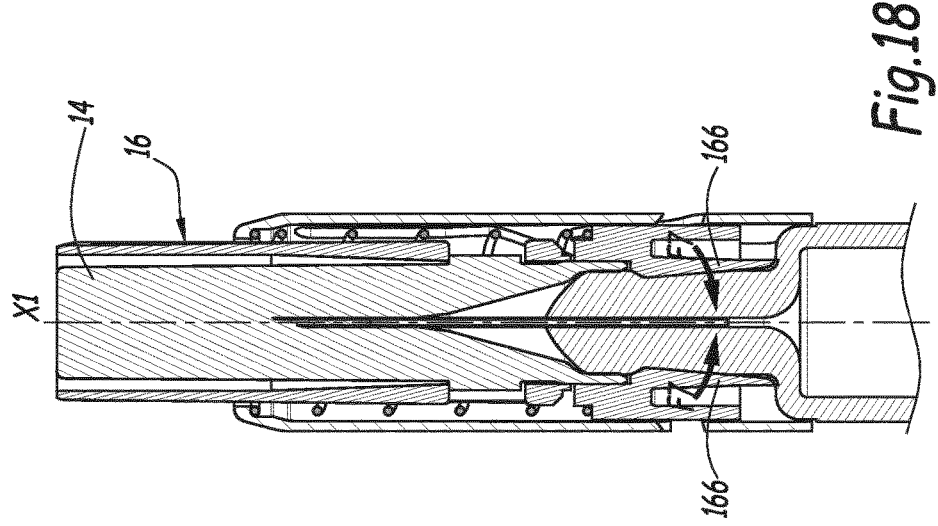
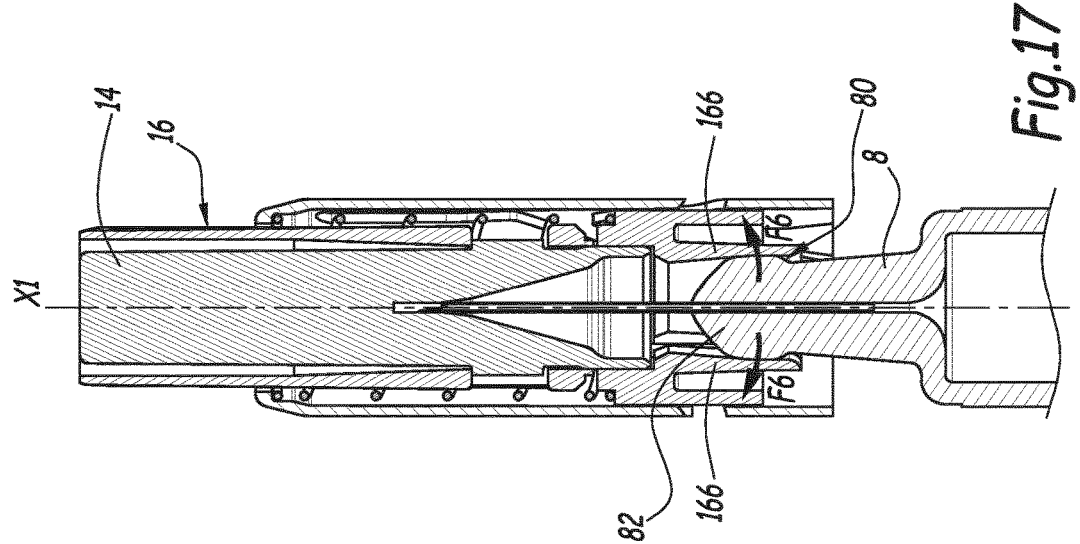
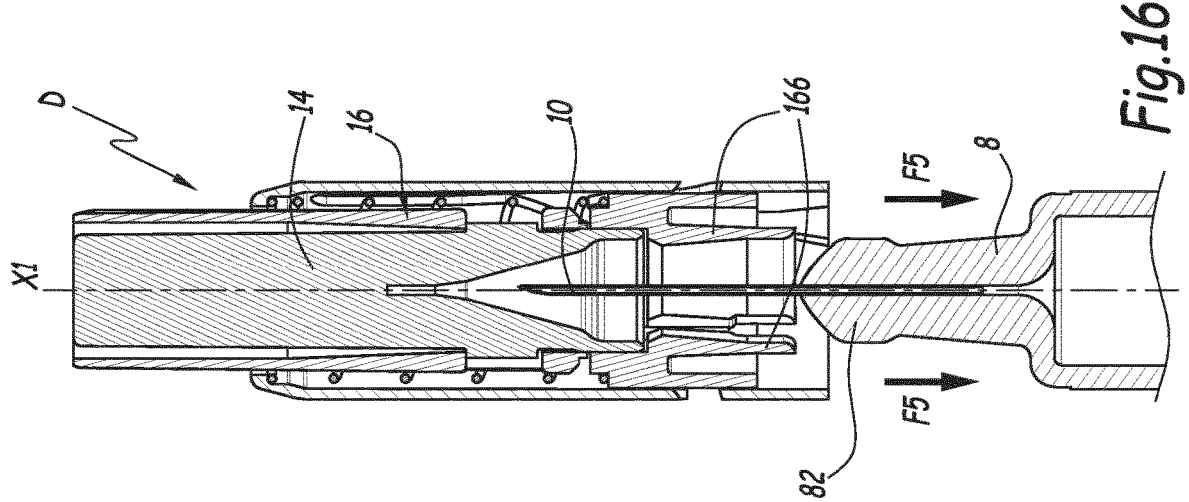

SYRINGE COMPRISING A BONDED NEEDLE

This application is a National Stage application of PCT International Application No. PCT/EP2016/064374, filed on Jun. 22, 2016 which claims the priority of French Application No. 1555748, filed on Jun. 23, 2015, both of which are incorporated herein by reference in their entirety.

The present invention relates to a syringe with a bonded needle, in particular a pre-filled syringe.

WO-A-2013/134 465 discloses a bonded needle syringe equipped with a needle guard. This needle guard is a soft tip into which the needle is inserted. Its function is to keep the needle clean, i.e. to avoid contamination of an active ingredient contained in the syringe body, while protecting the needle against any external mechanical action. The syringe also comprises an after-use safety system, whose function is to protect the needle at the end of the injection. This helps to avoid the user being injured by the needle when it is removed from the patient's body, and thus to fight against the transmission of diseases, such as HIV.

The safety system comprises an outer sleeve which is movable along a longitudinal axis of the syringe against an elastic force generated by a spring, between an advanced position where it covers the needle, and a retracted position where the needle is uncovered. The safety system also comprises a collar, which is mounted to rotate about an end portion of the syringe body. This collar comprises a pin engaged in a radial opening of the sleeve that forms a guide for the pin. During an injection, the sleeve bears against the patient's skin and can no longer rotate about its axis of revolution to guide the pin in the opening. The fact that the collar is mounted to rotate about the end portion of the syringe body thus allows the pin to be guided in the opening of the sleeve, although the latter is immobile in rotation about its axis.

With the material described in WO-A-2013/134 465, a poorly trained user may rotate the outer sleeve about its axis, thereby causing the collar to rotate about the end portion of the syringe body. The flexible tip is attached to the collar, so that it rotates together with the collar. Material chips may therefore penetrate inside the needle and contaminate the active ingredient during injection because the hollow needle has a beveled end.

In addition, a radial clearance is defined between the collar and the end portion of the syringe body to allow rotation of the collar. Therefore, there is also a radial clearance between the flexible tip and the end portion of the syringe body. Bacteria may thus infiltrate through this radial clearance into the internal volume of the tip, i.e. near the needle. These bacteria may then enter the needle when the tip is removed.

The invention more particularly intends to remedy these drawbacks by proposing a syringe with a bonded needle with which the risks of contamination of the active ingredient are reduced.

To this end, the invention relates to a bonded needle syringe, comprising a syringe body, a needle guard comprising a flexible tip, an outer sleeve that is movable along a longitudinal axis between an advanced position where it covers the needle, and a retracted position where it does not cover the needle, and a collar that is mounted with a radial clearance around an end portion of the syringe body, and which comprises at least one pin engaged in a guide opening of the sleeve. According to the invention, a portion of the flexible tip fills the radial clearance between the end portion of the syringe body and the collar when the tip is mounted on the syringe, so that the collar is immobilized in rotation around the end portion of the syringe body as the tip is mounted on the syringe.

By virtue of the invention, the tip is arranged so that there is sufficient adhesion to prevent the collar from rotating around the tip when it is mounted on the needle. Thus, the outer sleeve of the safety system is also locked in rotation about its axis until the flexible tip has been removed from the needle, which thus limits the risk of contamination.

According to advantageous but non-mandatory aspects of the invention, a bonded needle syringe may include one or more of the following features, taken in any technically feasible combination:

The portion of the flexible tip is compressed radially between the end portion of the syringe body and the collar when the needle guard is mounted on the syringe;

The needle guard comprises a rigid sleeve enveloping the flexible tip;

The sleeve is in two parts that are detachable from each other by a relative rotational movement between the two parts, or by a relative axial movement between the two parts, while the collar forms a first portion of the sleeve;

A radial clearance exists between the flexible tip and the second portion of the sleeve;

The tip and the sleeve are linked in translation parallel to the longitudinal axis;

The sleeve comprises two opposite annular shoulders which delimit between them a receiving volume of an annular bead belonging to the flexible tip;

The collar comprises attachment tabs on the syringe body, wherein these tabs do not oppose the rotation of the collar about the end portion of the syringe body when the tip is removed from the needle;

The syringe comprises means for locking the sleeve in an advanced position at the end of the injection.

The syringe is a pre-filled syringe.

Figure 2:
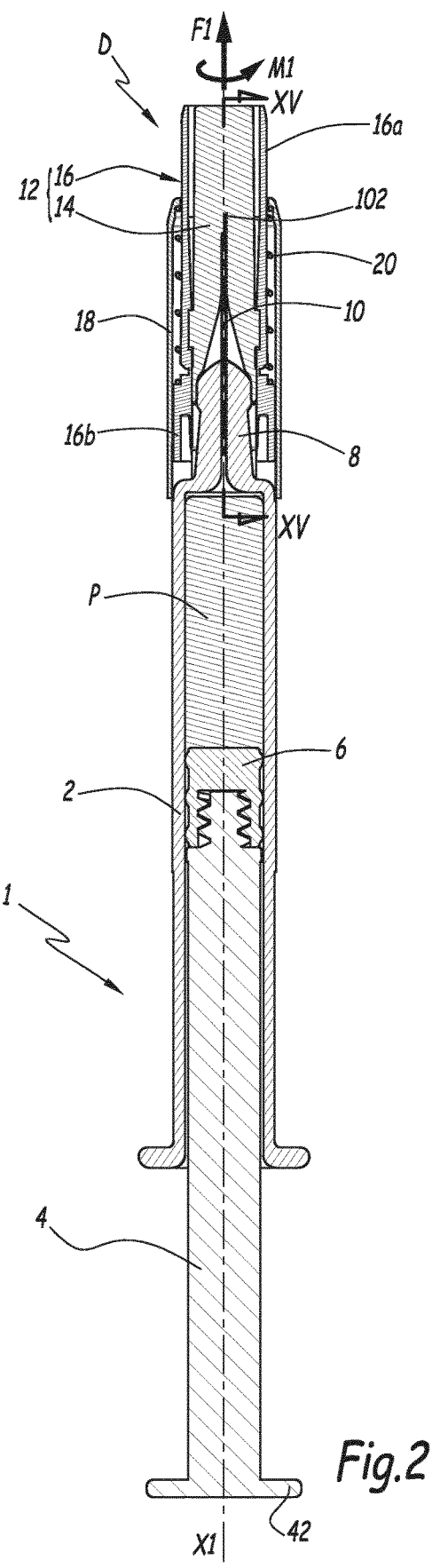
Figure 15:
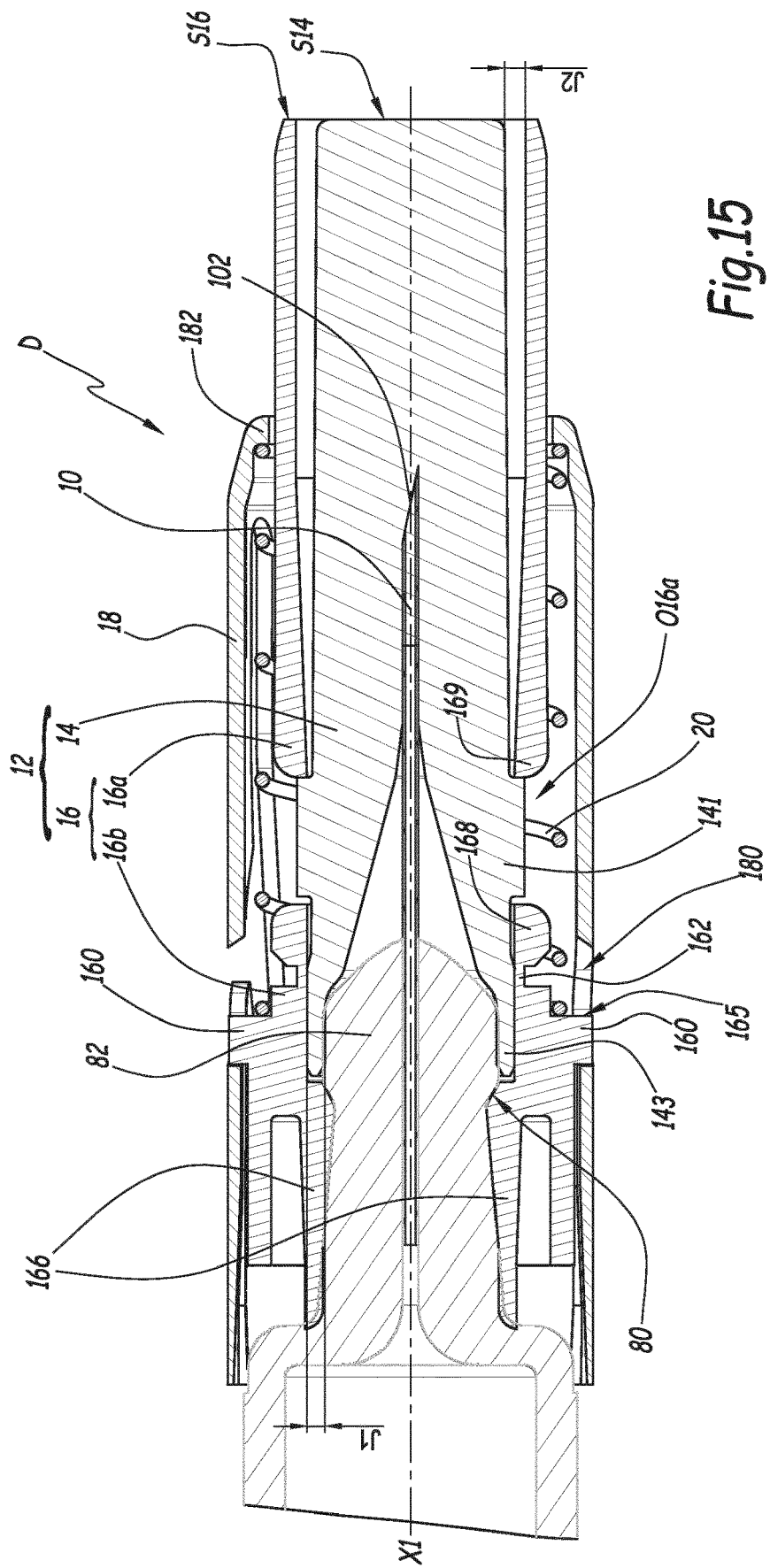

The invention and its other advantages will appear more clearly in the light of the following description of an embodiment of a bonded needle syringe according to its principle, given solely by way of example and with reference to the accompanying figures:

FIGS. 1, 3, 5, 7, 9, 11 and 13 each show a side view of a bonded needle syringe according to the invention, during a particular injection step, FIGS. 2, 4, 6, 8, 10, 12 and 14 each show a longitudinal section of the syringe corresponding to the figures mentioned above, FIG. 15 shows a longitudinal partial section on a larger scale along the line XV-XV in FIG. 2;

FIGS. 16 to 18 show longitudinal sections illustrating assembly steps of the device of FIG. 15 on a bonded needle syringe.

Each of the FIGS. 1 to 14 shows a syringe with a bonded needle 1. This syringe 1 is of the pre-filled type and extends along a longitudinal axis X1. It comprises a syringe body 2 of glass, which is generally tubular and centered on the axis X1. The body 2 comprises a syringe nose 8 having an external recess 80. The syringe nose 8 comprises a distal end portion 82 which extends from the external recess 80.

A hollow needle 10 is bonded inside an axial hole passing through the nose 8 that opens into the internal volume of the syringe body 2, in which an active ingredient P, such as a medicament, is stored. The needle 10 comprises a distal end 102 that is beveled.

The syringe 1 also comprises a piston rod 4 which is linked in translation with a seal 6. More precisely, the rod 4 comprises a threaded end which is screwed inside a thread provided in the seal 6. The seal 6 serves as a piston for ejecting the active ingredient P through the hollow needle 10, which is why the seal 6 is commonly called a "piston" or "piston seal". At the opposite axial end of the seal 6, the rod 4 comprises a shoulder 42 on which the user may exert a thrust force towards the nose 8. The rod 4 is displaceable in translation relative to the body 2 along the axis X1, i.e. it is able to slide inside the syringe body 2.

In this description, the forward or distal direction designates a direction parallel to the longitudinal axis X1 and faces the epidermis of the patient under normal conditions of use of the syringe 1, while the rear or proximal direction is oriented away from the patient opposite to the injection area on the side of the shoulder 42.

The syringe 1 comprises, at the front, a device D for protecting the needle 10. This device D is designed to be mounted on the nose 8 of the syringe 2. The device D comprises a needle guard 12 which allows, on the one hand, keeping the needle clean before use of the syringe 1 and, on the other hand, protecting the needle 10 against any external mechanical action. For example, the needle guard 12 prevents the needle 10 from bending or breaking before use.

The needle guard 12 is rigid and comprises a flexible tip 14 into which the needle 10 may be inserted and a rigid sleeve 16 which surrounds the tip 14. The tip 14 is made of elastomer, for example rubber or injectable thermoplastic material, while the rigid sleeve 16 is made of plastic, high density polyethylene (HDPE) in the case of the example. The needle guard 12 is more visible in FIG. 15. As may be seen in this figure, the endpiece 14 has an annular bead 141 and a skirt 143 surrounds the end portion 82 of the nose 8 at the back of the bead.

The rigid sleeve 16 is in two parts 16a and 16b which are detachable from each other by a relative rotational movement between these two parts. In fact, the two parts of the sleeve 16a and 16b are interconnected by breakable bridges 162, designed to be broken upon the application of a torque M1 through relative rotation between the two sleeve parts 16a and 16b. The part 16a is arranged in front of part 16b. The parts 16a and 16b are each tubular in shape and centered on the longitudinal axis X1.

The tip 14 and the front part 16a of the sleeve 16 are linked in translation along the axis X1. In fact, the bead 141 projects radially inside a peripheral housing O16a formed on the inner radial surface of the portion 16a. This peripheral housing O16a is delimited by two shoulders 168 and 169 axially opposite each other. As may be seen in FIG. 15, the housing O16a opens outwards from the sleeve 16 over part of the circumference of this sleeve. On the part of the sleeve visible in FIG. 2, the housing O16a does not open outwards from the sleeve 16. The opening character of the housing O16a is optional.

The tip 14 may be mounted from the front inside the sleeve 16 by temporarily compressing the bead 141. There is a radial clearance J2 between the outer surface of the tip 14 and the inner surface of the part 16a of the sleeve 16. As the tip 14 has a diameter that decreases forwards, the corresponding radial clearance J2 decreases backwards. The tip 14 is arranged inside the part 16a so that it is not integral in rotation with the latter. Furthermore, the front end axial surfaces S14 and S16, respectively of the tip 14 and the sleeve 16, are flush with one another.

The rear part 16b of the sleeve 16 forms a collar which snaps around the nose 8 of the syringe 1. The collar 16b thus comprises fixing means around the nose 8 of the syringe 1 formed by elastic tabs 166 shaped to clamp in the recess 80 of the nose 8. These tabs 166 do not oppose the rotation of the collar 16b about the end portion 82 of the syringe body 2 when the tip 14 is removed from the needle. The collar 16b also comprises two diametrically opposed pins 160, which protrude radially outwards with respect to the longitudinal axis X1. There is a radial clearance J1 between the collar 16b and the end portion 82 of the nose 8.

When the tip 14 is in place on the syringe 1, the skirt 143 of the tip 14 fills the radial clearance J1 between the collar 16b and the end portion 82 of the nose 8. More specifically, the skirt 143 is compressed radially between the end portion 82 and the collar 16b. This makes it possible to ensure sealing between the internal volume of the tip 14 and the outside, and thus prevent the infiltration of bacteria in the vicinity of the needle, as could happen with the material of WO-A-2013/134 465. In addition, the adhesion between the endpiece 14 and the collar 16b prevents it from rotating about the end portion 82 of the nose 8. On the other hand, as soon as the endpiece 14 is removed from the syringe 1, the collar 16b is free to rotate about the nose 8 due to the radial clearance J2 existing between the two parts.

The protection device D also includes an after-use safety system, which has the function of protecting the needle at the end of the injection. This safety system comprises an outer sleeve 18 that is arranged coaxially around the rigid sleeve 16. The sleeve 18 is made of opaque material to completely hide the needle 10. This sleeve 18 defines an internal radial edge 182 at its front end, and two openings 180 in which the pins 160 respectively engage. In the example, the pins 160 do not protrude outside the openings 160. The openings 180 serve as a guide for the pins 160. Each opening 180 is generally asymmetrically Y-shaped, with the branches of the Y extending rearwards. The branches of the Y are referenced 180a and 180c, while its central portion is referenced 180b. This central portion 180b is a straight portion, i.e. a passage. The device D also comprises means for locking the sleeve 18 in the advanced position, wherein these means are activated at the end of the injection. In the example, these locking means are formed by a housing 180d extending forwards from the branch 180c.

The outer sleeve 18 is axially movable, i.e. along the axis X1, between an advanced position where it covers the needle 10, and a retracted position where the needle 10 is uncovered. The safety system comprises elastic means to return the outer sleeve 18 to the advanced position. These return means comprise a helical spring 20 which is interposed between the internal axial flange 182 of the sleeve 18 and a shoulder 165 formed on the rear part 16b of the rigid sleeve 16. The coil spring 20 coils to the right, i.e. the winding direction of the spring 20 is to the right. This means that the spring 20 coils to the right, or clockwise, when looking at the spring 20 from the bottom in FIGS. 1 to 14, i.e. the rear side.

The various steps of use of the syringe 1 are described below with reference to FIGS. 1 to 14.

First, the user must remove the rigid needle guard 12 to be able to perform the injection. To do this, the user applies the torque M1 about the axis X1, as shown in FIG. 2 in order to rotate the front part 16a relative to the rear part 16b and break the bridges 162. This is possible because the rear part 16b of the sleeve 16, i.e. the collar, is immobile in rotation about the nose of the syringe 8 due to the adhesion with the skirt 143 of the tip 14. Once the bridges 162 have been broken, the user may remove the front part 16a of the rigid sleeve 16, as represented by the arrow F1 in FIG. 2. The removal of the part 16a causes the integral withdrawal of the end piece 14 through interaction of the bead 141 with the rear shoulder 168 of the housing O16a.

The collar 16*b* may then freely rotate about the nose 8 because the radial clearance J1 is no longer filled by the skirt 143 of the tip 14. The tip 14 and the front part 16*a* of the sleeve 16 are removed from the syringe 1 in a translation along the arrow F1, without rotating the tip 14 about the needle 10, so that the distal end 102 of the needle 10 that is beveled, does not form chips of material that may penetrate into the needle 10.

Figures 3, 4:
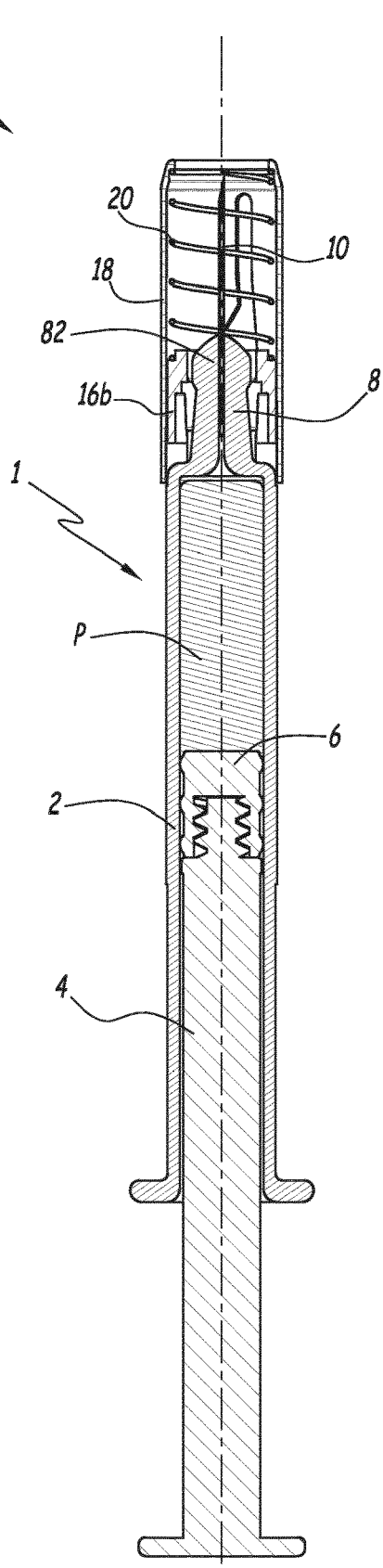

Removal of the tip 14 and the front part 16*a* of the sleeve 16 brings the syringe 1 to the configuration shown in FIGS. 3 and 4. In this configuration, the needle 10 is completely covered by the sleeve 18. As the syringe 1 has not been used, the pins 160 of the rear part 16*b* of the sleeve 16 are housed in the branch 180*a* of the recesses 180.

Referring to FIGS. 5 and 6, when the syringe 1 is brought against the epidermis of a patient, the adhesion between the front end of the sleeve 18 and the skin prevents the sleeve 18 from rotating about its axis. The pressure exerted by the sleeve 18 on the skin causes the sleeve 18 to recoil, as represented by the arrows F2 in FIG. 6. The spring 20 is then compressed, the needle 10 penetrates the epidermis, and the pins 160 move from the branch 180*a* to the central portion 180*b*. The displacement of the pins 160 inside the openings 180 is possible because the collar 16*b* carrying the pins 160 is free to turn about the nose 8.

The sleeve 18 then moves back around the syringe body 2 and the needle 10 is not uncovered until the syringe 1 is applied to the epidermis of the patient, unlike the materials according to WO-A-2013/134 465 and WO-A-2007/077 463 where the needle is partially uncovered before the syringe is applied to the patient's body. In other words, the sleeve 18 is not moved back before injection to uncover the needle 10. Thus, there is no risk of accidental puncture before injection. Continued movement brings the outer sleeve 18 to its retracted position, in which it no longer covers the needle 10. Continuation of the movement is carried out until the pins 160 reach the bottom of the passage 180*b* of the recesses 180, as shown in FIGS. 7 and 8.

Figure 7:
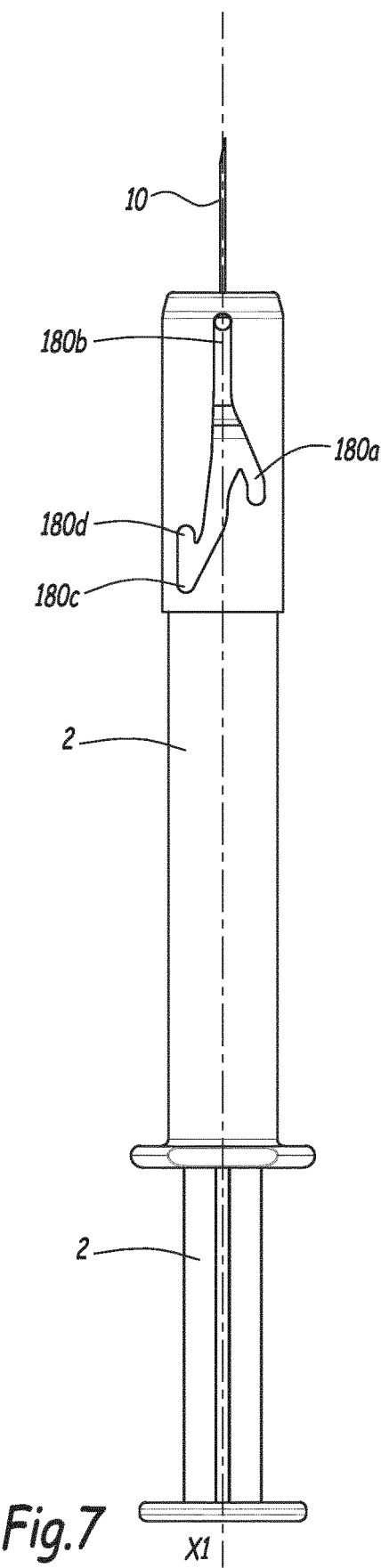
Figure 8:
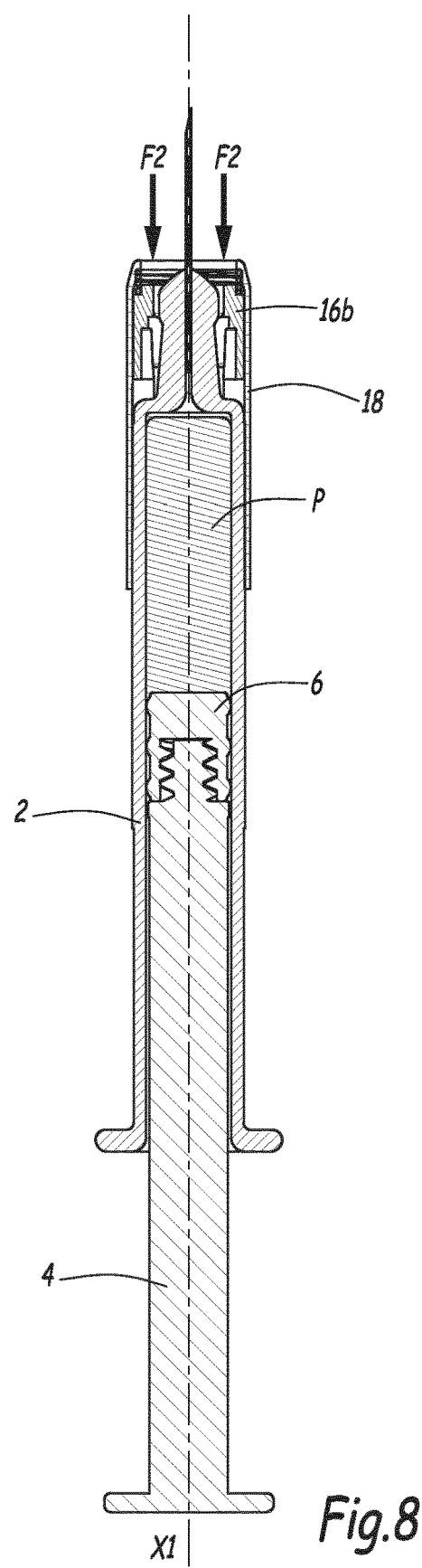
Figure 11:
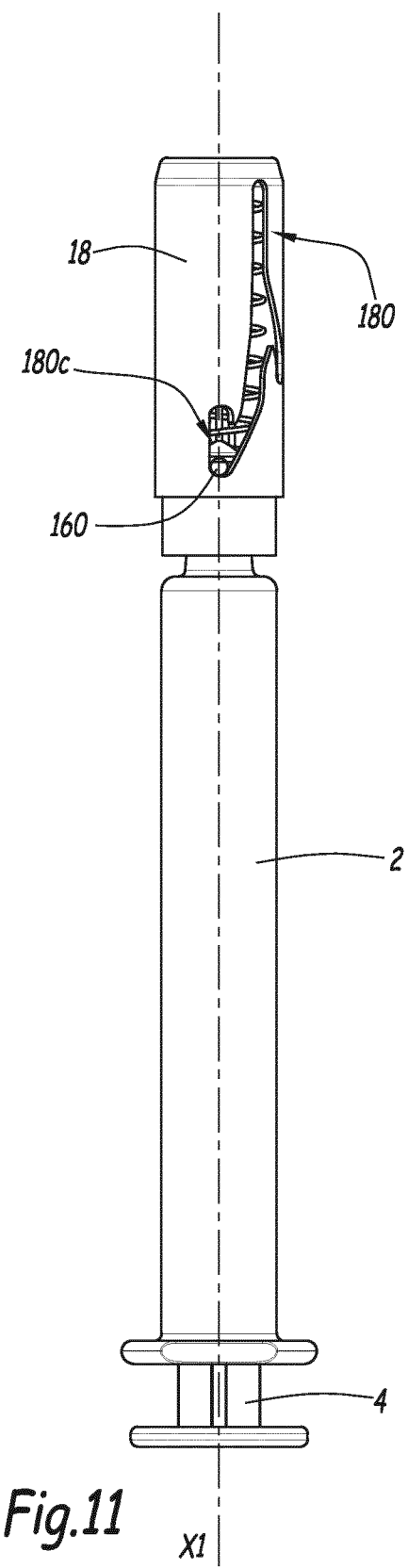
Figure 12:
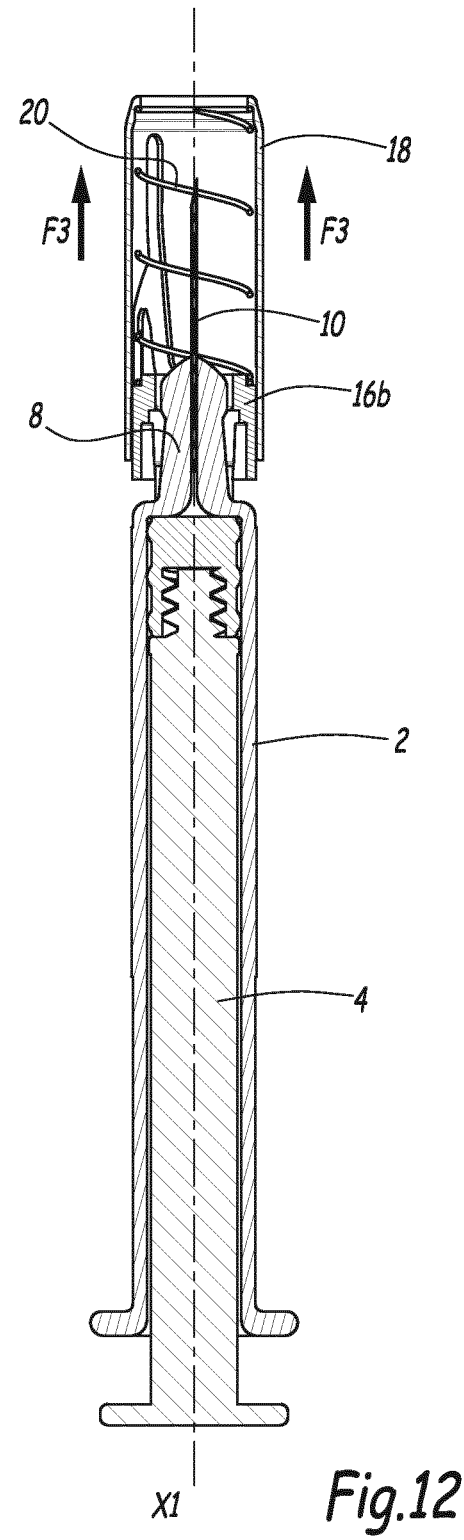

In the configuration of FIGS. 7 and 8, the needle 10 of the syringe 1 fully penetrates the epidermis of the patient. The user may then press the shoulder 42 of the rod 4 to eject the active ingredient P contained inside the syringe 1 into the body of the patient, as represented by the arrow F4 in FIG. 10.

When the user removes the syringe 1 from the body of the patient, the outer sleeve 18 is resiliently returned to the advanced position by the spring 20, as represented by the arrows F3 in FIG. 10. The outer sleeve 18 then returns to cover the needle 10 and the pins 160 slide in the passage 180*b* of the recesses 180 in the direction of the branch 180*c*. The syringe 1 is then in the configuration shown in FIGS. 11 and 12, which corresponds to an end-of-injection configuration.

If, after use of the syringe 1, an awkward user presses on the sleeve 18, i.e. tries to move the sleeve 18 back, the pins 160 then move into the housing 180*d* of the recesses 180 and the displacement of the sleeve 18 to the rear is blocked, as shown in FIGS. 13 and 14. This is an additional safety measure since the needle 10 can not be uncovered at the end of the injection. More specifically, the movement of the pins 160 of the branch 180*c* towards the housing 180*d* is favored because the winding direction of the spring 20 is to the right. In fact, this spring 20 exerts, when compressed, a torque on the sleeve 18 which is directed, because of its winding direction, in the counterclockwise direction in the plan view in FIG. 11. i.e. when looking at the syringe 1 from the side of the needle 10. This combination prevents the pins 160 from returning towards the passage 160*b* if the user tries to move the sleeve 18 back after the injection. This combination also makes it possible to correctly guide the pins 160 in the passage 180*b* to the branch 180*c* of the recesses 180, since the spring 20 exerts a torque on the collar 16*b* which is directed, because of its winding direction, in the clockwise direction in the plan view in FIG. 9, i.e. when looking at the syringe 1 on the side of the needle 10.

FIGS. 16 to 18 show the steps for mounting the protection device D on the nose 8 of the syringe body 2. A first step for mounting the protection device D consists in bringing the device D closer to the nose 8, as represented by the arrow F5 in FIG. 16. By continuing the movement in the direction of the arrow F5, the elastic tabs 166 are then deformed in a centrifugal radial direction F6 in contact with the nose 8, as may be seen in FIG. 17. Once the tabs 166 have passed the recess 80 of the nose 8, they snap against it by elastic return of the material, as represented by the arrows F7 in FIG. 18. The nose 8 of the syringe 1 is shaped to block the release of the tabs 166.

In a variant (not shown), return means other than a spring may be conceived to return the outer sleeve 18 to the advanced position at the end of the injection.

In a variant (not shown), a single recess 180 may be formed in the sleeve 18. Similarly, the sleeve may define a number of recesses 180 strictly greater than two, for example equal to three.

In a variant (not shown), the parts 16*a* and 16*b* of the sleeve 16 may be screwed into one another or linked by another rotary locking mechanism, for example of the bayonet type. In all cases, the parts 16*a* and 16*b* are detachable from each other by a relative rotational movement between the two parts.

Alternatively, the rod 4 and the seal 6 may be dissociated, i.e. the rod 4 is simply provided to push the seal 6.

According to another variant (not shown), the two parts 16*a* and 16*b* of the sleeve 16 are detachable from each other by a relative axial movement between the two parts. For example, the front part 16*b* may be detached from the collar 16*a* simply by pulling the part 16*b* away from the collar 16*a* or by tilting the part 16*b* with respect to the collar 16*a*, i.e. by offsetting the part 16*b* relative to a central axis of the collar 16*a*.

The characteristics of the variants and embodiments described above may be combined with each other to generate new embodiments according to the invention.

The invention claimed is:

1. A syringe with a bonded needle, comprising:
    a body of the syringe,
    a needle guard, comprising a flexible tip,
    an outer sleeve, which is movable along a longitudinal axis between an advanced position where the outer sleeve covers the bonded needle, and a retracted position where the outer sleeve does not cover the bonded needle, and
    a collar, which is mounted with a radial clearance around an end portion of the body, and which comprises at least one pin engaged in a guide opening of the outer sleeve,
    wherein a part of the flexible tip fills the radial clearance between the end portion of the body and the collar when the flexible tip is mounted on the syringe such that the part of the flexible tip contacts an outer peripheral surface of the end portion of the body and contacts an inner peripheral surface of the collar, so that the collar is immobilized in rotation about the end portion of the body as long as the flexible tip is mounted on the syringe.

2. The syringe according to claim 1, wherein the part of the flexible tip is compressed radially between the end portion of the body and the collar when the needle guard is mounted on the syringe.

3. The syringe according to claim 1, wherein the needle guard comprises a rigid sleeve enveloping the flexible tip.

4. The syringe according to claim 3, wherein the rigid sleeve and the collar are detachable from one another by a movement of relative rotation between the collar and the rigid sleeve, or by relative axial movement between the collar and the rigid sleeve.

5. The syringe according to claim 4, wherein a radial clearance exists between the flexible tip and the rigid sleeve.

6. The syringe according to claim 3, wherein the flexible tip and the rigid sleeve are linked in translation parallel to the longitudinal axis.

7. The syringe according to claim 6, wherein the rigid sleeve comprises two opposite annular shoulders which delimit between them a volume for receiving an annular bead belonging to the flexible tip.

8. The syringe according to claim 1, wherein the collar comprises tabs for attachment to the body, wherein these tabs do not oppose the rotation of the collar about the end portion of the body when the flexible tip is removed from the bonded needle.

9. The syringe according to claim 1, comprising means for locking the outer sleeve in the advanced position at the end of an injection.

10. The syringe according to claim 1, wherein the syringe is a pre-filled syringe.

11. The syringe according to claim 1, wherein the collar is disposed within the outer sleeve.

* * * * *